United States Patent [19]

Krause et al.

[11] Patent Number: 5,225,333
[45] Date of Patent: Jul. 6, 1993

[54] PROCESS AND APPARATUS FOR THE DETECTION OF TOXICITY IN SURFACE WATERS AS WELL AS DRINKING WATER AND INDUSTRIAL WATER

[76] Inventors: Hans Krause, Elisabethenstr. 14b, 6350 Bad Nauheim; Helmut Maske, Kronshagener Weg 34, 2300 Kiel, both of Fed. Rep. of Germany

[21] Appl. No.: 190,576

[22] Filed: May 5, 1988

[30] Foreign Application Priority Data

May 6, 1987 [DE] Fed. Rep. of Germany ....... 3715114

[51] Int. Cl.⁵ .................. C12Q 1/18; C12Q 1/02; G01N 21/64
[52] U.S. Cl. ...................................... 435/32; 435/291; 435/29; 435/808; 435/946; 436/52; 436/805; 250/458.1; 422/82.08
[58] Field of Search .................. 435/29, 32, 291, 808, 435/946; 436/52, 805; 250/458.1; 422/82.08

[56] References Cited

U.S. PATENT DOCUMENTS 4,295,199 10/1981 Curry et al. ..................... 364/555
4,303,410 12/1981 Copeland ......................... 23/230 R
4,778,763 10/1988 Makiguchi et al. .................. 436/47

OTHER PUBLICATIONS

Morgun, V. N., et al., Biological Abstracts, vol. 82, No. 2, Abstract No. 17528 (1986).
Tsvylev, O. P., et al., Chemical Abstracts, vol. 91, No. 25, Abstract No. 205290v (1979).
Lavergne, J., et al., Chemical Abstracts, vol. 93, No. 23, Abstract No. 218086z (1980).

*Primary Examiner*—Esther L. Kepplinger
*Assistant Examiner*—Toni R. Scheiner
*Attorney, Agent, or Firm*—Weingarten, Schurgin, Gagnebin & Hayes

[57] ABSTRACT

This invention provides a process and an apparatus for the detection of toxicity in surface waters, by which the fluorescence of a water sample is measured in that the correlation, especially the ratio, between the prompt fluorescence and retarded fluorescence of the water sample is determined, which contains a toxicity-sensitive bioorganism. The apparatus comprises a combination of a first fluorescence measuring means for measuring prompt fluorescence and a second fluorescence measuring means for measuring retarded fluorescence as well as a signal correlation means for correlating the output signals of two fluorescence measuring means with each other to form an output quantity indicating the toxicity of the water sample.

22 Claims, 4 Drawing Sheets

PROCESS AND APPARATUS FOR THE DETECTION OF TOXICITY IN SURFACE WATERS AS WELL AS DRINKING WATER AND INDUSTRIAL WATER

DESCRIPTION

This invention relates to a process for the detection of toxicity in surface waters as well as drinking water and industrial water, in which the fluorescence of a water sample is measured. Moreover, this invention relates to an apparatus for the detection of toxicity in surface waters as well as drinking water and industrial water, comprising a fluorescence measuring means for measuring the fluorescence of liquids.

As can be taken from the section "Wasseruntersuchungen mit Hilfe von Toxizitätstests" by W. K. Besch in the book "Limnologie für die Praxis", editor Besch, Hamm, Lenhardt, Melzer, Scharf, Steinberg, Landsberg/Lech, 1984, the classical bases of toxicity tests made in flowing waters are physicochemical measuring methods or bioassays with cultivated organisms or organisms kept in ponds, such as, for example, algae, bacteria, crustaceans, insects or fish. The disadvantage of each of these classical measuring methods is that it requires many apparatus and/or is very time-consuming. Moreover, statements made as to toxicity, which result from bioassays, can only be made after several hours or even after one or two days as is indicated in the book "Gewässer- und Pflanzenschutz" by F. Meinck published in the paper series of the Association of Water, Soil and Air Hygiene, Vol. 37, Gustav Fischer Verlag, Stuttgart 1972 and in the section "Toxizitätstest mit Goldorfe und Zebraberbling" by W. K. Besch, B. W. Scharf and E. Mayer, published in the book "Wassergefährdende Stoffe" by L. Roth (editor), ecomed, Landsberg/Lech, 1985.

A later method of detecting herbicides in flowing waters, set forth in the publication "Use of Algal Fluorescence for an Automated Biological Monitoring System" by G. Benecke, W. Falke and W. Schmidt in Bull. Environm. Contam. Toxicol. 28, 1982, pages 385 to 395, is based on the analysis of fluorescence induction curves with standard algae cultures to the effect that the prompt fluorescence on the whole increases by about the factor of two as a result of the contamination with herbicides. The analysis of prompt fluorescence induction curves required in this case requires a lot of calculations and the interpretation of the analysis results is still not unambiguous and depends on the experimental marginal conditions, especially on temperature, pretreatment with light and the general physiological condition of the algae.

The process and apparatus which are set forth in DE-OS 34 12 023 and serve for rapid determination of harmful substances in waters by means of a biomaterial with the capability of photosynthetic primary processes are also based on the analysis of fluorescence induction. In this case, the biomaterial used is thylacoids of higher plants cultivated under standardized conditions, the cell homogenates of which are separated by centrifugation and freeze-dried, and the biomaterial is used in charges of the same basic activity together with inorganic and/or organic stabilizers as a suspension in standardized samples. The harmful substances are determined in a measuring medium by measuring the fluorescence induction at two times of a period of the exposure of the standardized sample containing the biomaterial, the distances of which times being determined, and by comparing the difference of the measured values with the set difference values. This analysis method requires the extremely time and labor-consuming production of a cell homogenate sample analyzed as to the evolution of oxygen and fluorescence induction, only the prompt fluorescence being measured. As compared to the above-mentioned analysis of fluorescence induction curves with standard algae cultures this disadvantageously implies an even stricter specialization with respect to the sample substance, since in this case no algae cultures are generally used but rather special cell homogenates of thylacoids of higher plants. Although as compared to the above-mentioned analysis of fluorescence induction curves the calculations required are considerably reduced by the process according to DE-OS 34 12 023 in that only two measuring points can be chosen from the fluorescence induction curve, the expressiveness of the process is restricted considerably by this, so that the process is only a rough one. Moreover, no continuous measurement is possible. Furthermore, L. O. Björn published investigations on the abating kinetics of retarded fluorescence depending on a herbicide effect in the periodical "Photochem. Photobiol." 1971, 13, pages 5 to 20. In this case as well, the interpretation of the results obtained is not unambiguous. Although retarded fluorescence decreases with the damage and/or destruction of photosynthesis, the relative change depends on the time window of the retarded fluorescence measurement, in which measurements are made after stopping the stimulation as can be taken from the doctoral thesis "Verzögerte Fluoreszenz photoautotropher Algen" by H. Krause, University of Regensburg, 1986.

It is particularly the object of the present invention to prove or detect herbicides and other toxic substances in waters rapidly, continuously and with great temporal disintegration and relatively few apparatus regarding their toxic effect.

This object is solved by a process of the type mentioned in the beginning in that the correlation between prompt fluorescence and retarded fluorescence of a water sample is determined, which contains a toxicity-sensitive bioorganism.

Moreover, this object is solved by an apparatus of the type mentioned in the beginning, which has a fluorescence measuring means for measuring the fluorescence in liquids and is characterized according to the invention in that the fluorescence measuring means comprises a combination of a first fluorescence measuring means for measuring prompt fluorescence and a second fluorescence measuring means for measuring retarded fluorescence and that a signal correlation means is subsequently connected to the common output of the two fluorescence means for correlating their output signals.

Although, as explained above, neither the analysis results of prompt fluorescence render possible an unambiguous statement on toxicity nor the analysis of retarded fluorescence permits an unambiguous interpretation of toxicity, it was surprisingly found within the scope of the present invention that the correlation value, especially the ratio between the prompt fluorescence and retarded fluorescence of a water sample represents a clear measure of the toxicity of this water sample.

Intensive investigations made by the inventors within the scope of the present invention, showed that although prompt and retarded fluorescences vary considerably during the day due to the adaptation of light, this variation is rather synchronous and has roughly the same relative amplitude, so that the correlation, especially the ratio, of the value, especially the intensity, of the prompt fluorescence relative to the value, especially the intensity, of retarded fluorescence hardly varies. Variations in the correlation, especially the ratio, of the two fluorescence values, i.e. the value of prompt fluorescence and the value of retarded fluorescence, relative to each other can thus be interpreted as disturbances of cell physiology, i.e. normally as contaminations.

Thus, starting from the above surprising inventors' findings, the present invention is based on the proposal to infer the effect of toxic components in the water on a bioorganism in the water, especially a bioorganism naturally occurring in the water, preferably phytoplankton, from simultaneously measuring prompt and retarded fluorescences, i.e. especially their intensities, at suitable periods of time with one or more measuring points and from comparing the fluorescence intensities of the measuring points, especially by an algorithm.

As to the technical feasibility of the toxicity detection according to the invention both spatial separation, e.g. by using a continuous flow system, and temporal separation, e.g. by using the light pulse method may be used.

Thus, this invention proposes to evaluate the two fluorescence components, especially the intensity of prompt fluorescence and the intensity of retarded fluorescence, in relation to each other, since their signal intensities show opposed tendencies in the case of contamination. Although each individual signal shows relative variations depending on the previous illumination as is given for example by the progression of daylight, the correlation value, especially the ratio, of the two signals to each other is roughly constant.

In particular, the process according to this invention distinguishes itself in that the correlation between the prompt fluorescence and retarded fluorescence of a water sample containing a toxicity-sensitive bioorganism is determined and compared with the corresponding correlation determined with a non-contaminated sample.

The process can be especially carried out such that the correlation is measured within a predetermined time window starting from the end of influence of the stimulating light for retarded fluorescence on the sample, this time window preferably having a width of from 0.1 to 10 seconds and preferably being within a range of from 0.5 to 500 seconds after the end of influence of the stimulating light for retarded fluorescence.

Industrial water and drinking water without a suitable natural stock of bioorganisms, especially without a natural stock of phytoplanktons, can nevertheless be investigated as to toxic components in that the water sample is mixed, for example, with a culture solution of a toxicity-sensitive bioorganism, especially a phytoplankton culture solution.

When determining the corresponding correlation between prompt and retarded fluorescences of a non-contaminated water sample, it can be determined by conventional methods such as, for example, mass spectrometry or chromatography whether the water sample is actually not contaminated. This correlation can be made a standard by measurements with a non-contaminated sample and used for actual measurements to be carried a long time later.

As the above statements show, a plankton advantageously proved to be useful as a toxicity-sensitive bioorganism, i.e. especially a phytoplankton. The toxicity-sensitive bioorganisms used may also be bacteria or dinoflagellates.

A preferred embodiment of the process according to the invention distinguishes itself in that prompt and retarded fluorescences, especially their intensities, is stimulated by means of light having the same wavelength. The advantage thereof is that only a single light source is required for stimulating prompt and retarded fluorescences. Light having a wavelength range around 440 nm or light having a wavelength range around 660 to 685 nm may be preferably used for stimulating prompt and retarded fluorescences, especially when using phytoplankton as the toxicity-sensitive bioorganism.

However, it is also possible to stimulate prompt and retarded fluorescences by means of light having different wavelengths thereby advantageously permitting a simpler disturbance-free separation of the two fluorescence measurements, i.e. the measurement of prompt and retarded fluorescences. In this case it is preferred to stimulate prompt fluorescence by means of light having a wavelength range of around 440 nm and/or 660 to 685 nm and retarded fluorescence by means of light having a wavelength range of around 700 to 730 nm, especially when using phytophlankton as the toxicity-sensitive bioorganism.

Regarding the measurement of fluorescence, especially the intensity of the fluorescence radiation, it is possible to measure both prompt and retarded fluorescences in the same wavelength range and prompt and retarded fluorescences in different wavelength ranges, i.e. in the latter case to measure prompt fluorescence in a wavelength range differing from that of retarded fluorescence. In the former case, for example, prompt and retarded fluorescences may both be measured in the wavelength range around 685 nm, while in the latter case measurements can be made such that prompt fluorescence is measured in the wavelength range around 730 nm and retarded fluorescence is measured in the wavelength around 685 nm.

The apparatus for the detection of toxicity in surface waters provided by the invention can be developed either as a flow-through measuring means in the continuous flow system of the water sample, whereby a spatial separation between the measuring system for measuring prompt fluorescence and the measuring system for measuring retarded fluorescence results, or the apparatus can be developed such that it has a common measuring system for measuring prompt and retarded fluorescences, in which prompt and retarded fluorescences are stimulated and/or measured one after the other, e.g. by light pulses, thereby resulting a temporal separation of the two fluorescence measurements.

In the former case, i.e. with spatial separation of the fluorescence measurements, the apparatus according to the invention preferably distinguishes itself by two fluorescence measuring flow-through cells arranged in series with respect to flow, the connecting line of which contains a light trap and, viewed in the direction of flow, to the first fluorescence measuring flow-through cell of which a first light detector is assigned for measuring prompt fluorescence and, viewed in the direction of flow, to the second fluorescence measuring flow-through cell of which a second light detector is assigned for measuring retarded fluorescence.

In this case, with respect to the light source the development can be such that (a) a light source for stimulating prompt and retarded fluorescences is assigned to the first fluorescence measuring flow-through cell, or (b) a first light source for stimulating prompt fluorescence is assigned to the first fluorescence measuring flow-through cell and, with respect to flow, a fluorescence stimulating flow-through cell is arranged between the first and second fluorescence measuring flow-through cells, to which a second light source is assigned for stimulating retarded fluorescence, whereby the light trap may be provided in the connecting line between the fluorescence stimulating flow-through cell and the second fluorescence measuring flow-through cell.

In both of the above-mentioned embodiments another light trap may be provided in the outlet line of the second fluorescence measuring flow-through cell.

In the case of temporal separation of the fluorescence measurements the apparatus according to the invention is preferably developed such that it has a common fluorescence measuring cell for measuring prompt and retarded fluorescences and these two types of fluorescence can be measured temporally one after the other, whereby the joint fluorescence measuring cell may also be a flow-through cell which is then, however, operated discontinuously in flow-through, i.e. is filled with the sample in a first flow-through time, then the flow-through is discontinued and the fluorescence is measured and thereafter the just measured sample is removed from the flow-through cell in the flow-through and the cell is e.g. filled with a new sample.

The above-mentioned as well as further advantages and features of the invention are detailed hereinafter with reference to FIGS. 1 to 7 of the drawing by means of some, particularly preferred embodiments of the process and apparatus according to the invention:

Figure 1:
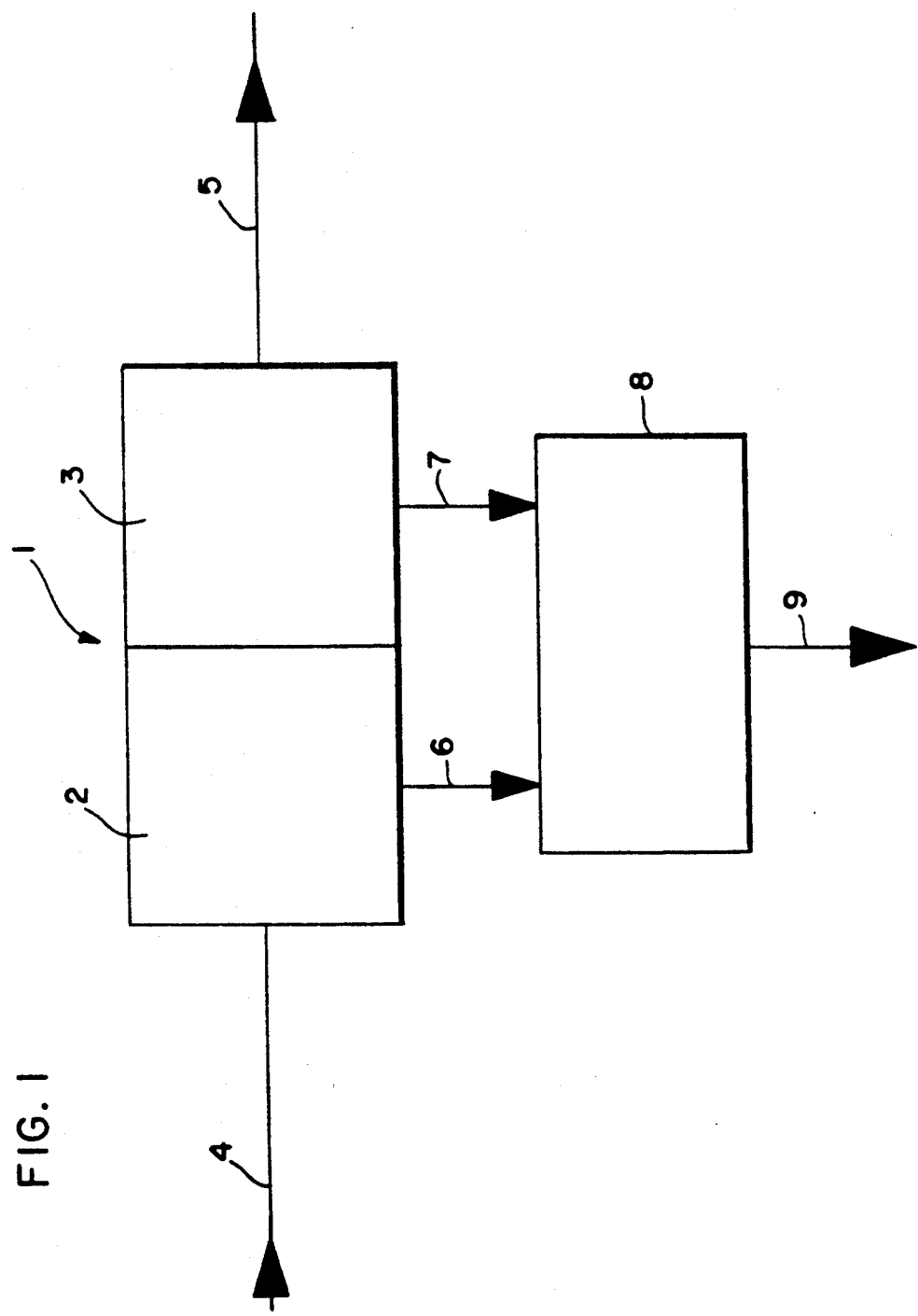
FIG. 1 shows a first embodiment of an apparatus according to the invention, in which the intensities of prompt and retarded fluorescences are measured in different places according to the flow-through method, the apparatus being shown schematically in a block diagram.
Figure 2:
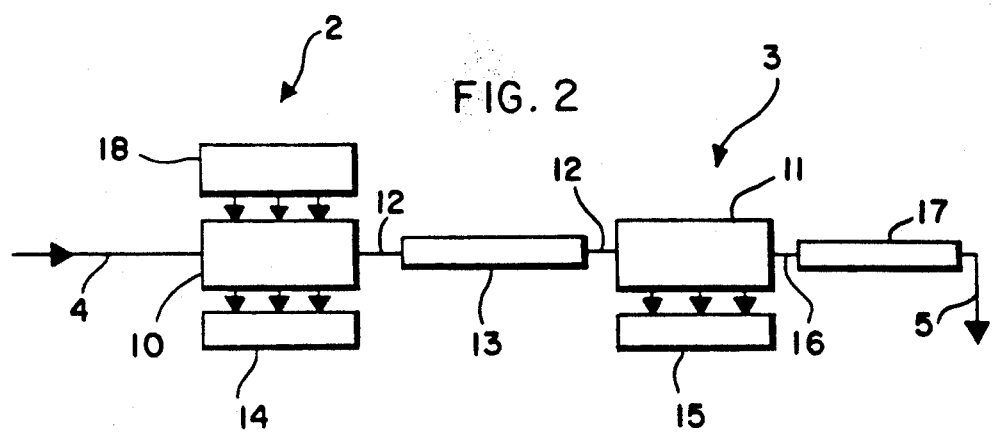
FIG. 2 shows a first variant of the arrangement of the fluorescence measuring flow-through cells, the light source and the light detectors, which may be used in the apparatus according to FIG. 1.
Figure 4:
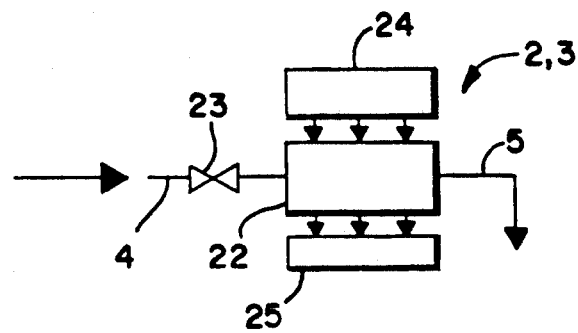
Figure 5:
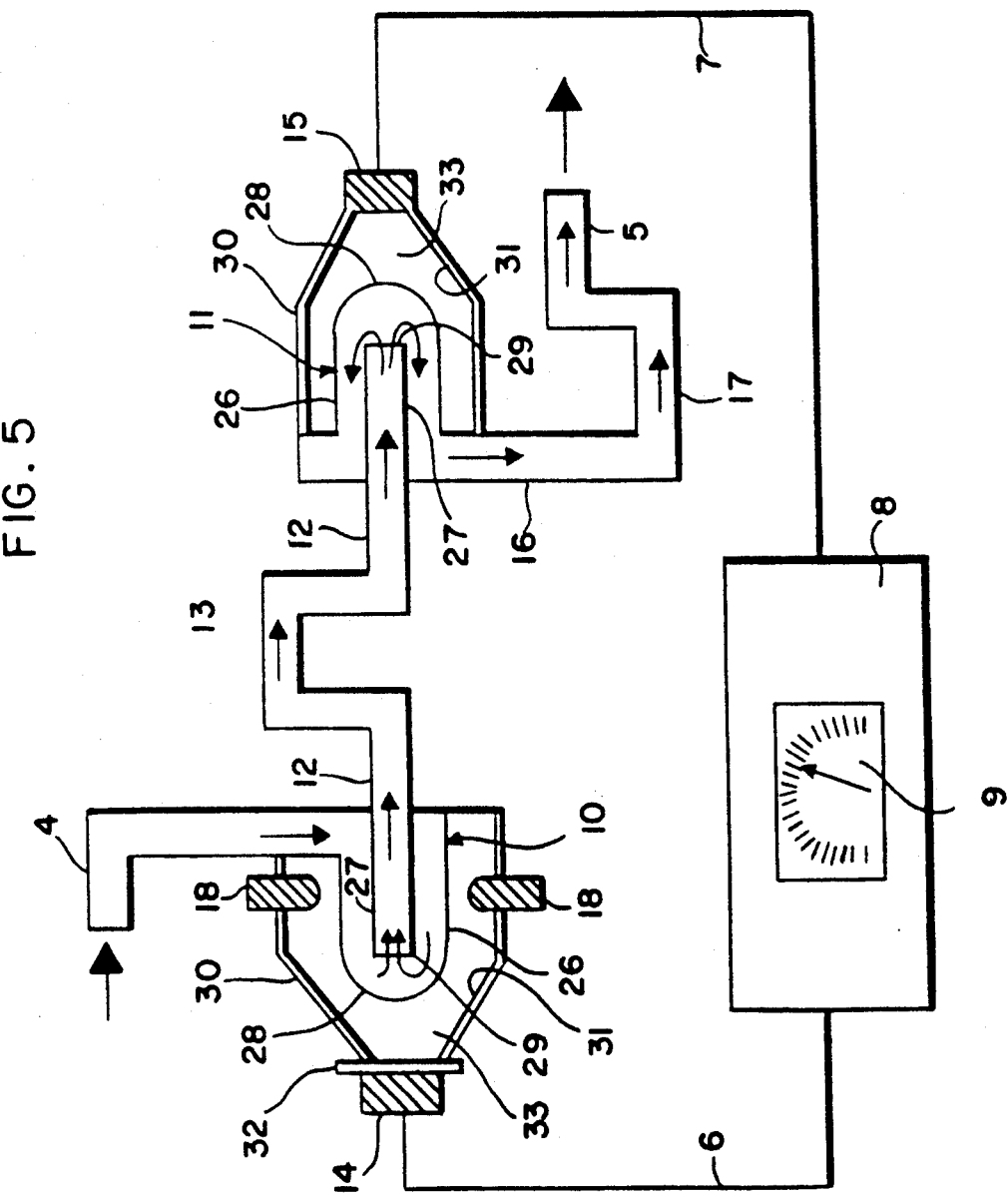
Figure 6:
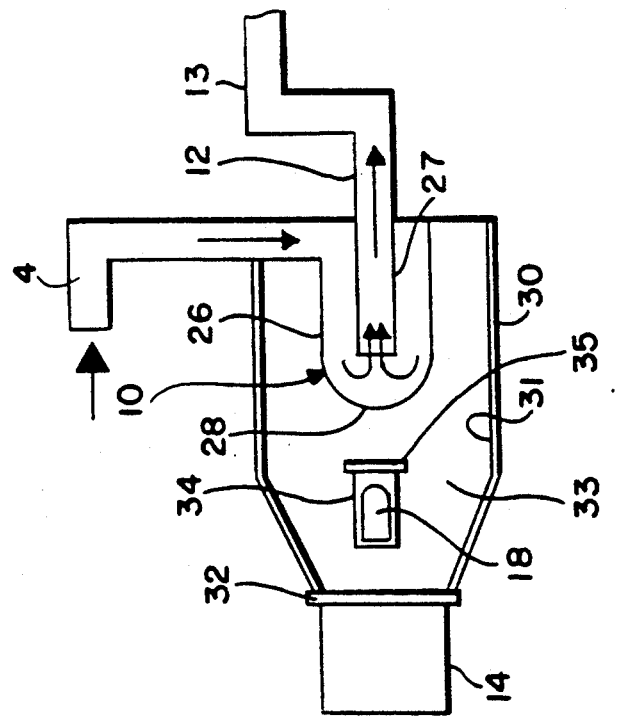

FIG. 4 shows an arrangement of the fluorescence measuring cell, the light source and the light detector for an embodiment of the apparatus according to the invention, in which the fluorescence measurements are made at different times; and FIG. 5 shows a more detailed embodiment of an apparatus according to FIG. 1 of the invention having an arrangement of the fluorescence measuring flow-through cells, the light source and the light detectors according to FIG. 2;

FIG. 6 shows the left-hand top of FIG. 5 in a first modified embodiment; and

Figure 7:
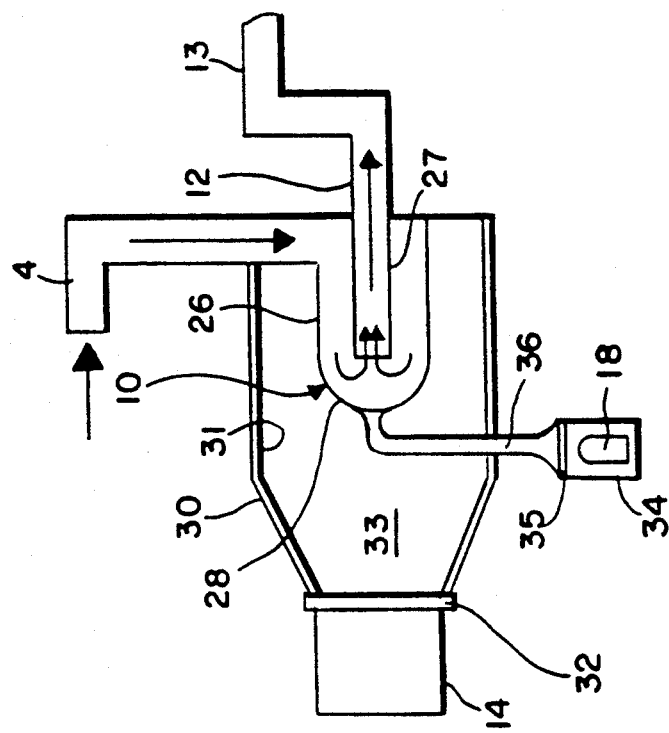

FIG. 7 shows the left-hand top of FIG. 5 in a second modified embodiment.

First of all, reference is made to FIG. 1, in which the fundamental design of an apparatus for the detection of toxicity in surface waters, which is operated in the continuous flow system, is illustrated. This apparatus comprises a fluorescence measuring means 1 for measuring the fluorescence of liquids. This fluorescence measuring means 1 is a combination of a first fluorescence measuring means 2 for measuring prompt fluorescence and a second fluorescence measuring means 3 for measuring retarded fluorescence. A measuring sample flows through these two fluorescence measuring means 2 and 3 one after the other, the measuring sample supply having the reference numeral of 4 and the measuring sample outlet having the reference numeral of 5. The measuring signal output 6 of the fluorescence measuring means 2 for prompt fluorescence and the measuring signal output 7 of the fluorescence measuring means 3 for retarded fluorescence at which measuring signals representing the intensity of prompt and/or retarded fluorescence appear, are both connected with the signal input or the signal inputs of their common signal correlation means 8 correlating the two measuring signals applied by an algorithm with each other, so that an output quantity is obtained at the output 9 of this signal correlation means 8, which is a clear measure of the toxicity of the measuring sample.

In the simplest case, the algorithm may be the quotient of the two measuring signals appearing at the measuring signal output 6 and 7, so that the arithmetic ratio of these two measuring signals is obtained at the output 9 as the starting value for toxicity.

In the embodiment of the apparatus in which the measurement of prompt and retarded fluorescences is carried out in a common measuring system temporally one after the other, the fluorescence measuring means 2 and the fluorescence measuring means 3 are combined to form a single fluorescence measuring means having a common, single measuring signal output at which the measuring signals for prompt and retarded fluorescences are received temporally one after the other, however the signal correlation means 8 being developed in the same way as explained above and operating by correlating the measuring signals for prompt and retarded fluorescences obtained temporally one after the other, in the same way with one another.

In the last-mentioned embodiment, however, a separate light detector each for measuring prompt fluorescence and for measuring retarded fluorescence may be assigned to the common fluorescence measuring cell, in which case the same arrangement will then result with respect to the measuring signal outputs 6 and 7 as illustrated in FIG. 1.

Figure 3:
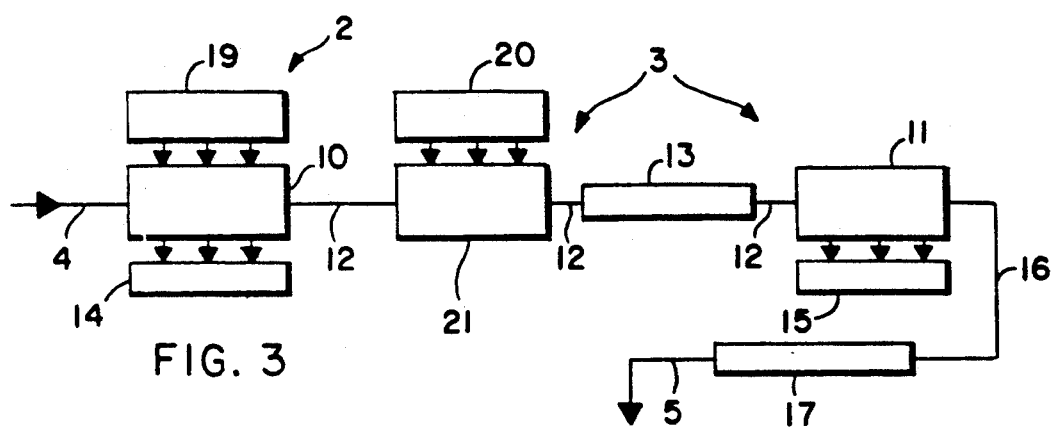
FIG. 3 shows a second variant of the arrangement of the fluorescence measuring flow-through cells, the light sources and the light detectors, which may be used in the apparatus according to FIG. 1.

FIGS. 2 and 3 are now dealt with in detail. They show two different embodiments of the fluorescence stimulating and measuring arrangement, which may both be used in the measuring means according to FIG. 1 if it is operated according to the continuous sample flow-through method, like parts having the same reference numbers as in FIG. 1, with respect to which reference is made to the above statements regarding FIG. 1 to avoid repetitions. In both the embodiment of the apparatus according to FIG. 2 and the embodiment of the apparatus according to FIG. 3 two fluorescence measuring flow-through cells 10 and 11 arranged one after the other with respect to flow are provided, whose connecting line 12 for supplying the liquid sample from the first fluorescence measuring flow-through cell 10 to the second fluorescence measuring flow-through cell 11 contains a light trap 13. Viewed in the flow direction of the liquid sample, a first light detector 14 is assigned to the first fluorescence measuring flow-through cell 10 for measuring prompt fluorescence, and, viewed in the flow direction of the liquid sample, a second light detector 15 is assigned to the second fluorescence measuring flow-through cell 11 for measuring retarded fluorescence. Finally, in both cases a further light trap 17 is arranged in the outlet line 16 of the second fluorescence measuring flow-through cell 11, through which the liquid sample is removed from the measuring system.

The essential difference between the two embodiments of FIGS. 2 and 3 is the following:

(a) In the embodiment according to FIG. 2 a common light source 18 is provided for stimulating prompt and retarded fluorescences, which, of course, is assigned to the first fluorescence measuring flow-through cell 10.

(b) In contrast thereto, two light sources are provided in the embodiment according to FIG. 3, i.e. a first light source 19 for stimulating prompt fluorescence, which, of course, is assigned to the first fluorescence measuring flow-through cell 10, and a second light source 20 for stimulating retarded fluorescence, which is assigned to a fluorescence stimulating flow-through cell 21 provided in the connecting line 12 between the first fluorescence measuring flow-through cell 10 and the first light trap 13.

Finally, FIG. 4 shows an embodiment of the apparatus, which has a common fluorescence measuring cell 22 which is adapted to be operated, e.g. via a flow-through valve 23, in discontinuous flow-through of the liquid sample and to which a light source 24 for stimulating prompt and retarded fluorescences as well as a light detector 25 for measuring prompt and retarded fluorescences are assigned. Reference is to be made to the fact that, although not illustrated in the drawing, the light source 24 may also consist of two separated light sources, one of which serving to stimulate prompt fluorescence and the other one serving to stimulate retarded fluorescence and/or that the light detector 25 may comprise a first light detector for measuring prompt fluorescence and a second light detector for measuring retarded fluorescence.

FIG. 5 details an embodiment of the apparatus for the detection of toxicity in surface waters according to FIG. 1, which has an arrangement of the fluorescence measuring flow-through cells 10 and 11, the light source 18 and the light detectors 14, 15 according to FIG. 2. With respect to the fundamental design, reference is thus made to the explanations according to FIGS. 1 and 2. Hereinafter, only the special features going beyond FIGS. 1 and 2 are explained:

As FIG. 5 shows the fluorescence measuring flow-through cells 10 and 11 are designed in this case according to the type of what is called a cooling trap consisting substantially of a cylindrical-cupular outer glass jar 26 and an inner glass tube 27 of smaller diameter, which is concentric thereto and the free end 29 of which is spaced opposite the rounded bottom 28 of the glass jar 26 and, in the one case, serves as an inlet opening for the sample liquid supplied to the outer glass jar 26, as is shown in the left-hand part of FIG. 5, while, in the other case, this free end 29 serves as an outlet opening for the liquid sample to be supplied to the outer glass jar 26 as is shown in the right-hand part of FIG. 5.

According to FIG. 5 the two fluorescence measuring flow-through cells 10 and 11 are surrounded concentrically by a cell housing 30 consisting in the present case of a cylindrical portion and a truncated cone-shaped portion and being provided with a metal-coat 31 on its inside, so that the fluorescence light irradiation is supplied to a very large extent to the light detector 14 and/or 15 provided at the size-reduced truncated cone and opposite the rounded bottom 28 by multiple reflection.

Light-emitting diodes are provided as a light source 18 for stimulating prompt and retarded fluorescences, and a filter 32 is arranged before the light detector 14, reference being made in this place to the fact that, if required, a corresponding light filter can also be provided before the light detector 15. Light traps 13 and 17 are developed as U-shaped sections of the connecting line 12 and/or the outlet line 16, but they may also have any other known suitable shape.

The output 9 of the signal correlation means 8 is represented in this case by an indicating instrument indicating the toxicity or non-toxicity of the liquid sample measured. Of course, a recorder output and/or any other output desired such as e.g. a printer or the like, may be connected or provided instead of the indicating instrument.

Preferred procedures for the detection of toxicity in surface waters are now to be explained by means of the above-explained apparatus:

Initially the stimulation wavelength for prompt and retarded fluorescences may be the same for the embodiments of the apparatus according to FIGS. 2 and 4, and be between 660 and 685 nm or within the range around 440 nm. In the former case the emission wavelength of prompt fluorescence is at about 730 nm and that of retarded fluorescence is wideband at 685 nm. In the latter case the emission wavelength of prompt and retarded fluorescences is at 685 nm. In the embodiment of the apparatus according to FIG. 3 different stimulation wavelengths for prompt and retarded fluorescences may be chosen, i.e. in addition to the above-indicated stimulation wavelengths for retarded fluorescence the range of the stimulation wavelength may be between 700 and 730 nm. These stimulation wavelengths apply especially when using phytoplankton as the toxicity-sensitive bioorganism.

In the continuous flow system according to FIG. 2 the liquid sample is pumped into the fluorescence measuring flow-through cell 10 where it is illuminated by the light source 18 and prompt fluorescence stimulated by this is measured by means of the light detector 14. The light trap 13 which may also consist of several parallel light traps serves to transport the liquid sample continuously into the fluorescence measuring flow-through cell 11 in which the retarded fluorescence is measured by means of the light detector 15. The liquid sample leaving the fluorescence measuring flow-through cell 11 flows through the other light trap 17 before it is discarded.

In the continuous flow system illustrated in FIG. 3 the prompt fluorescence is stimulated by means of the light source 19 in the fluorescence measuring flow-through cell 10 and it is measured by means of the light detector 14. The downstream fluorescence measuring cell 21 serves to stimulate retarded fluorescence by means of the light source 20, and the downstream fluorescence measuring flow-through cell 11 serves to measure retarded fluorescence by means of the light detector 15.

In the measuring system shown in FIG. 4, which operates according to the light pulse method in connection with a single fluorescence measuring cell 22, the liquid sample is conveyed discontinuously into the fluorescence measuring cell 22 where it is illuminated by the light source 24. At the same time, the prompt fluorescence is measured by means of the light detector 25. After switching off the light of the light source 24, the retarded fluorescence may be measured in the same fluorescence measuring cell 22 by means of the same light detector 25. Having finished this measuring cycle a new liquid sample may be fed into the fluorescence measuring cell by opening the flow-through valve 23.

In general, it is to be noted with respect to all of the embodiments of the proposed apparatus that the samples may be pretreated in the continuous flow system or by light pulses with strong exposure in order to bring them to a standard light adaptation status. Furthermore, a heater may be provided on the side where the liquid samples flow in for periodic heat pre-treatment, preferably above 50° C., of the samples to thus determine the zero point of retarded fluorescence as well as clean the cells.

In the apparatus developed according to FIG. 5, the liquid sample is pumped through a transparent tube, e.g. a glass tube, to the transparent fluorescence measuring flow-through cell 10 especially consisting of glass, into which the liquid sample flows tangentially and is supplied spirally to the detector end, i.e. the bottom 28, of the fluorescence measuring flow-through cell 10, while the liquid sample is illuminated by light-emitting diodes 18. The induced prompt fluorescence is emitted from the outer transparent jar 26, which may be particularly a glass jar, into the reflecting cell cavity 33 between the outer jar 26 and the cell housing 30 and reaches the light detector 14 through the light filter 32, which detector may be, for example, a photomultiplier or photo-sensitive diode and measures the intensity of prompt fluorescence. The liquid sample is then supplied through glass tube 27 and light trap 13 to the transparent bottom 28 of the fluorescence measuring flow-through cell 11, which is near the detector. From there the liquid sample is led off radially in fountain configuration, supplied through the light trap 17 and discarded. The retarded fluorescence emitted in the fluorescence measuring flow-through cell 11 is emitted in the reflecting cell cavity 33 and detected by the light detector 15 which may also be, for example, a photomultiplier or a photo-sensitive diode. The output signals of the two light detectors 14 and 15 are applied to the signal correlation means 8, whose output quantity indicates the toxicity degree of the liquid sample at the output 9.

The signal correlation means 8 may be an analog or digital computer and, in the simplest case, it is a device for forming a quotient or an analog or digital divider.

Whenever glass is mentioned as the material of components it may also be replaced by quartz or another transparent material such as, for example, plastics.

The light-emitting diodes mentioned, so-called LEDs, may be restricted spectrally by means of filters. The light-emitting diodes may be replaced by lamps or light guides which are supplied with light from lamps or light-emitting diodes.

While in the embodiment of FIG. 5 several light-emitting diodes 18 protrude into the cell cavity 33, in the embodiment of FIG. 6 a single light-emitting diode of relatively high radiation output is provided in a small housing 34 within the cell cavity 33 of the fluorescence measuring flow-through cell 10 for measuring prompt fluorescence. The housing 34 is arranged between the filter 32 and the bottom 28 of the glass jar 26 in such a way that its radiation outlet window formed by a filter 35 faces the bottom 28, whereas the housing 34 is otherwise impervious to light, so that the detector 14 is largely shielded from the stimulating light leaving via the filter 35. The prompt fluorescence light, however, readily reaches the detector 14 due to the metal-coat 31.

The embodiment of FIG. 7 differs from that of FIG. 6 substantially in that the small housing 34 is arranged outside the cell housing 30 and the light of the light-emitting diode located therein is supplied to the cell 10 after passage through the filter 35 by means of a light guide 36 in such a way that it is reflected by the bottom 28 in a direction diametrically away from the detector 14, the detector being also largely shielded from the stimulation light.

Of course lamps or other light sources may be used instead of the light-emitting diodes 18. The embodiment according to FIG. 7 may also be modified in such a way that the light guide 36 is omitted and the housing 34 is connected to the bottom 28 and/or the glass jar 26 via a filter 35 directly above the light well (not shown), which is recommended especially with a relatively large light source, i.e. when a lamp is provided instead of the light-emitting diode 18.

In this case, the two filters 32 and 35 make sure that the detector 14 does not receive to much stimulating light, i.e. the measurement of the emission light of prompt fluorescence is largely free from disturbances caused by the stimulating light.

It is preferred to chose the filters 32 and 35 in such a way that the flow-through curve of the two filters 32 and 35 is such that the amount of light still penetrating the two filters in series arrangement at $3\sigma$ ($\sigma$=half-width) is smaller than $10^{-3}$, preferably at $6\sigma$ smaller than $10^{-8}$, of the intensity of the stimulating light impinging on the filters at this spectral location. In this case, the stimulation wavelength is preferably about 665 nm and the emission wavelength of prompt fluorescence is about 730 nm. The above condition also applies to other $\Delta\lambda$ values, $\Delta\lambda$ being the difference between the wavelength of maximum emission transparence of prompt fluorescence and the wavelength of maximum stimulation transparence.

We claim:

1. A process for the detection of toxicity in water, comprising the steps of:
    stimulating a water sample containing a toxicity-sensitive bioorganism by means of light having at least one predetermined wavelength;
    measuring the intensity of prompt fluorescence in the light-stimulated water sample containing said bioorganism;
    providing an output value corresponding to the measured intensity of prompt fluorescence;
    measuring the intensity of delayed fluorescence of the light-stimulated water containing said bioorganism synchronously with said measuring of prompt fluorescence intensity;
    providing an output value corresponding to the measured intensity of delayed fluorescence;
    correlating said output value corresponding to the measured intensity of prompt fluorescence with said value corresponding to the measured intensity of delayed fluorescence to obtain a correlated sample value; and
    providing an indication of said correlated sample value compared with a correlated sample value obtained from a non-contaminated sample, as a measure of the toxicity level of said light-stimulated water.

2. The process of claim 1 wherein said correlating step includes measuring within a predetermined time window starting from the end of influence of the stimulating light for the retarded fluorescence on the sample, this time window defined between 0.1 to 500 seconds after the end of said stimulating light for the retarded fluorescence.

3. The process of claim 1 wherein the toxicity-sensitive bioorganism is selected from the group consisting of planktons, phytoplanktons, bacteria and dinoflagellates.

4. The process of claim 1 wherein the light-stimulating step includes using light having at least two predetermined wavelengths.

5. The process of claim 1 wherein said light-stimulating step includes using light having a wavelength of 440 nm for stimulating prompt and retarded fluorescences.

6. The process of claim 1 wherein said light-stimulating step includes using light having a wavelength range between 660 nm to 685 nm for stimulating prompt and retarded fluorescences.

7. The process of claim 1 wherein the prompt and retarded fluorescences are stimulated by means of light having different wavelengths.

8. The process of claim 1 wherein the step of light-stimulating the water containing a toxicity-sensitive bioorganism includes stimulating by means of light having a wavelength 700 to 730 nm.

9. The process of claim 1 wherein the prompt and retarded fluorescences are measured in the same wavelength range.

10. The process of claim 1 wherein the prompt and retarded fluorescences are measured at 685 nm.

11. The process of claim 1 wherein the prompt and retarded fluorescences are measured in different wavelength ranges.

12. The process of claim 1 wherein the prompt fluorescence is measured at 730 nm and the retarded fluorescence is measured at 685 nm.

13. An apparatus for the detection of toxicity in water, comprising:
  a light source for light-stimulating water containing a toxicity-sensitive bioorganism;
  as first fluorescence measuring means for measuring prompt fluorescence of the light-stimulated water, said first measuring means having means for producing a signal output value corresponding to the measured intensity of prompt fluorescence;
  a second fluorescence measuring means for measuring retarded fluorescence of the water, said second measuring means having means for producing a signal output value corresponding to the measured intensity of retarded fluorescence; and
  a programmable common signal correlation means connected to said first and second fluorescence measuring means for receiving said signal output value corresponding to the measured intensity of prompt fluorescence and said signal output value corresponding to the measured intensity of retarded fluorescence, for correlating said signal output value corresponding to the measured intensity of prompt fluorescence with said signal output value corresponding to the measured intensity of delayed fluorescence to obtain a correlated sample value, and for providing an indication of said correlated sample value compared with a correlated sample value obtained from a non-contaminated sample, as a measure of the toxicity level of said light-stimulated water.

14. The apparatus according to claim 13 further comprising
  said first fluorescence measuring means having a flow-through cell;
  said second fluorescence measuring means having a flow-through cell;
  a connecting line for connecting said first and second flow-through cells;
  a first light detector located in said first flow-through cell for measuring the prompt fluorescence of water within said first flow-through cell; and
  a second light detector for measuring the retarded fluorescence of water within said second flow-through cell.

15. The apparatus of claim 14 further comprising a light source located within said first fluorescence measuring flow-through cell for stimulating prompt and retarded fluorescences.

16. The apparatus of claim 15 wherein
  a second light source is located in said second flow-through cell for stimulating retarded fluorescence.

17. The apparatus of claim 14 wherein
  a light trap is provided in said connecting line.

18. The apparatus of claim 13, wherein said first fluorescence measuring means and said second fluorescence measuring means are located in a common fluorescence measuring cell.

19. The apparatus of claim 14 wherein said second fluorescence measuring flow-through cell has an outlet line having a light trap.

20. The apparatus of claim 13 wherein the signal correlation means is a computer.

21. The apparatus of claim 13 wherein said signal correlation means provides a quotient of said two signal output values.

22. An apparatus for the detection of toxicity in water, comprising:
  a light source for light-stimulating water containing a toxicity-sensitive bioorganism;
  a fluorescence measuring means
    for measuring prompt fluorescence of the light-stimulated water and producing a first signal output value corresponding to the measured intensity of prompt fluorescence, and
    for subsequently measuring retarded fluorescence of the light-stimulated water and producing a second signal output value corresponding to the measured intensity of retarded fluorescence; and
  a programmable signal correlation means connected to said fluorescence measuring means
    for receiving sequentially said first and second signal output values,
    for correlating said received first and second signal output values to obtain a correlated sample value, and
    for providing an indication of said correlated sample value compared with a correlated sample value obtained from a noncontaminated sample, as a measure of the toxicity level of said light-stimulated water.

* * * * *